(12) United States Patent
Pruett

(10) Patent No.: US 8,590,546 B2
(45) Date of Patent: Nov. 26, 2013

(54) FLOSSING SYSTEM

(76) Inventor: Timothy J. Pruett, Tavares, FL (US)

( * ) Notice: Subject to any disclaimer, the term of this patent is extended or adjusted under 35 U.S.C. 154(b) by 13 days.

(21) Appl. No.: 13/065,228

(22) Filed: Mar. 17, 2011

(65) Prior Publication Data
US 2012/0234348 A1 Sep. 20, 2012

(51) Int. Cl.
*A61C 15/00* (2006.01)
(52) U.S. Cl.
USPC ........................................ 132/322; 132/323
(58) Field of Classification Search
USPC .............. 132/321–327, 329, 309; 206/63.5; 15/167.1, 207.2
See application file for complete search history.

(56) References Cited

U.S. PATENT DOCUMENTS

| | | | |
|---|---|---|---|
| 3,892,249 A * | 7/1975 | Jones et al. ................ | 132/323 |
| 4,235,253 A | 11/1980 | Moore | |
| 4,245,658 A | 1/1981 | Lecouturier | |
| 5,069,233 A | 12/1991 | Ritter | |
| 5,097,852 A * | 3/1992 | Wu ................................ | 132/309 |
| 5,170,809 A * | 12/1992 | Imai et al. ................ | 132/322 |
| 5,267,579 A * | 12/1993 | Bushberger ................ | 132/322 |
| 5,483,982 A * | 1/1996 | Bennett et al. ................ | 132/323 |
| 5,669,097 A * | 9/1997 | Klinkhammer ................ | 15/167.1 |
| 5,722,440 A | 3/1998 | Urso | |
| 5,769,102 A * | 6/1998 | Zebuhr ................ | 132/322 |
| 6,954,961 B2 * | 10/2005 | Ferber et al. ................ | 15/22.1 |
| 7,055,531 B2 | 6/2006 | Rehkemper | |
| 7,140,373 B2 * | 11/2006 | Rehkemper ................ | 132/322 |
| 7,174,904 B2 * | 2/2007 | Ochs et al. ................ | 132/323 |
| 7,311,108 B2 | 12/2007 | Getgey et al. | |
| 7,392,810 B2 | 7/2008 | Apotheker et al. | |
| 7,487,785 B2 * | 2/2009 | Dougan et al. ................ | 132/323 |
| 8,025,068 B2 | 9/2011 | Culver | |
| 2005/0076933 A1 * | 4/2005 | Getgey et al. ................ | 132/322 |
| 2005/0205107 A1 * | 9/2005 | Ochs ................ | 132/323 |
| 2006/0054180 A1 * | 3/2006 | Getgey et al. ................ | 132/322 |
| 2007/0054240 A1 * | 3/2007 | Masterman et al. ................ | 433/118 |
| 2008/0092917 A1 * | 4/2008 | Getgey et al. ................ | 132/322 |
| 2009/0165814 A1 * | 7/2009 | Welt et al. ................ | 132/323 |
| 2009/0293212 A1 * | 12/2009 | Junkins ................ | 15/22.1 |
| 2010/0139689 A1 * | 6/2010 | Couch ................ | 132/322 |
| 2012/0021382 A1 * | 1/2012 | Dickie ................ | 433/216 |

\* cited by examiner

*Primary Examiner* — Robyn Doan
*Assistant Examiner* — Tatiana Nobrega

(57) ABSTRACT

A handle has distal and proximal ends and an exterior surface. Controls with a vibrating coupler are adapted to vibrate rapidly in response to the controls. A head has a distal end and a proximal end. The proximal end has a coupling recess for receiving the vibrating coupler. The enlarged distal end has a generally planar surface and a generally hemispherical surface. The hemispherical surface has a recess to couple with a holder. A holder has a central base and two outwardly extending fingers. The fingers have free ends with a piece of floss secured between the free ends. Bristles extend from the planar surface between the fingers to control the movement of the floss between teeth.

1 Claim, 3 Drawing Sheets

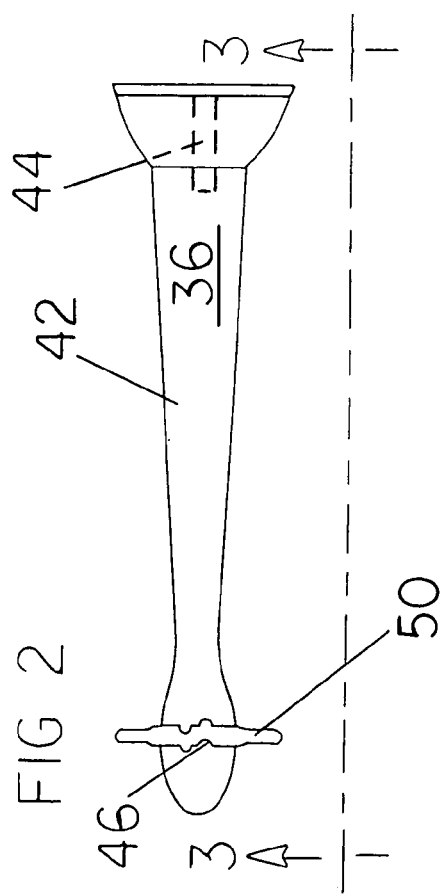
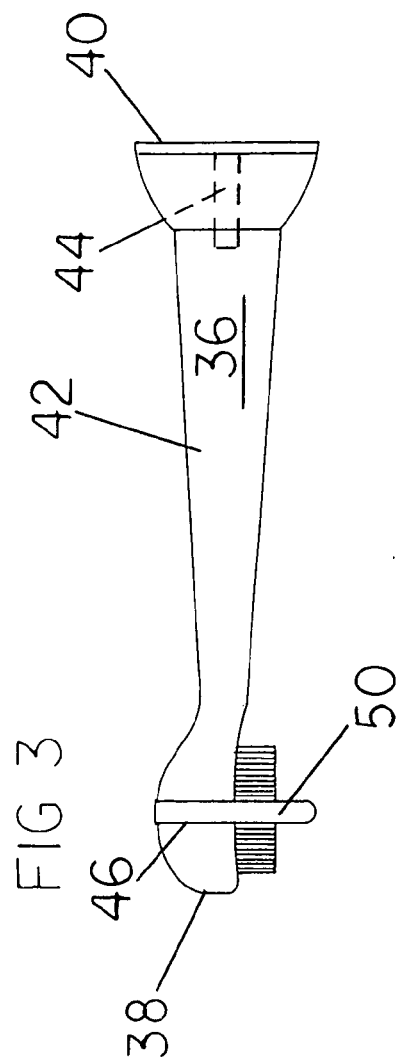

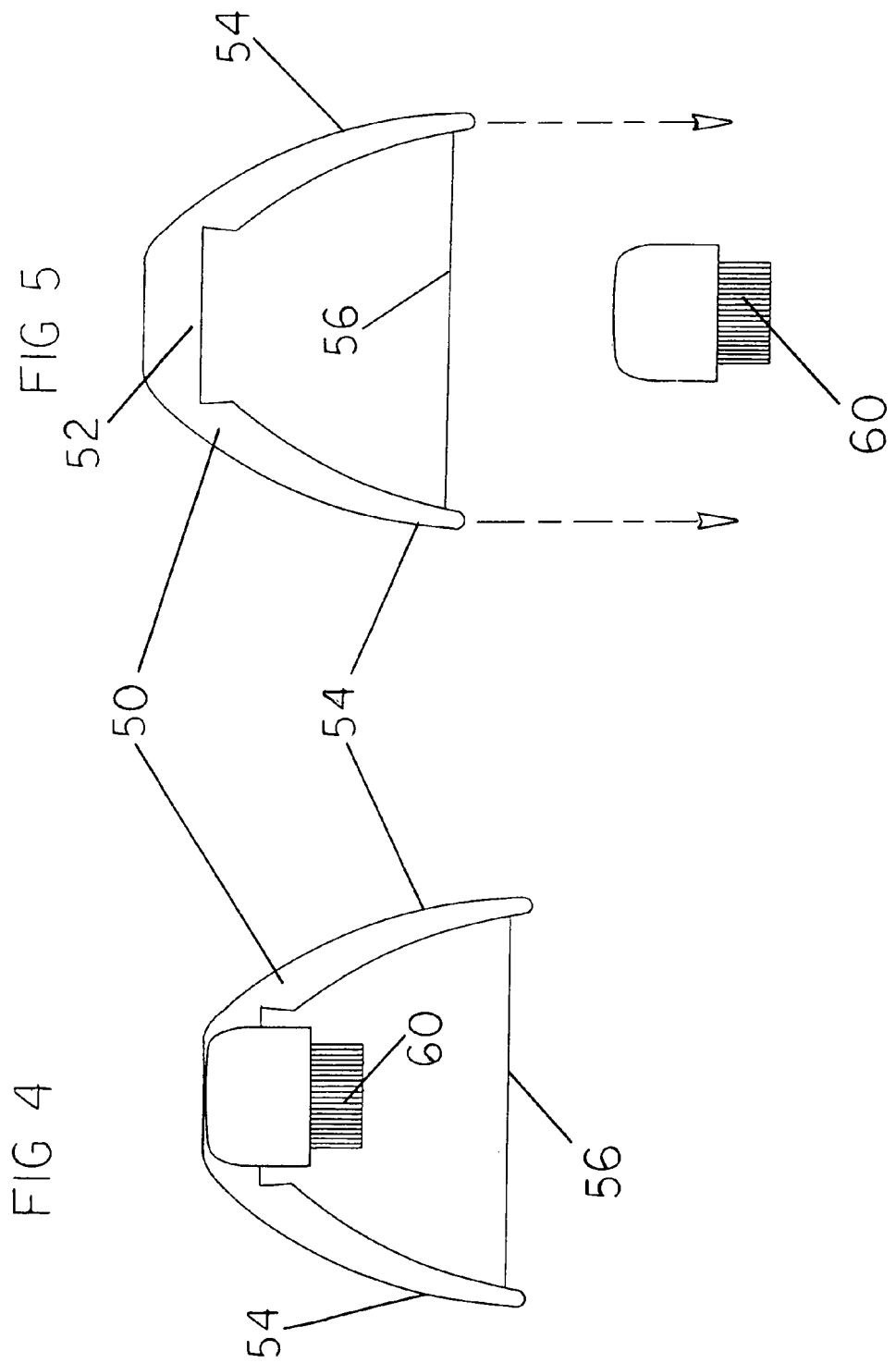

FLOSSING SYSTEM

BACKGROUND OF THE INVENTION

Field of the Invention

The present invention relates to a flossing system and more particularly pertains to cleaning teeth at regions between adjacent teeth of a user and for vibrating regions of the mouth of the user between teeth and gums, the cleaning and vibrating being done in a safe, painless, convenient, efficient and economical manner.

SUMMARY OF THE INVENTION

In view of the disadvantages inherent in the known types of teeth cleaning systems of known designs and configurations now present in the prior art, the present invention provides an improved flossing system. As such, the general purpose of the present invention, which will be described subsequently in greater detail, is to provide a new and improved flossing system and method which has all the advantages of the prior art and none of the disadvantages.

To attain this, the present invention essentially comprises a flossing system. First provided is a handle. The handle is in a generally cylindrical configuration. The handle has a distal end. The handle has a proximal end. The handle has an exterior surface. The exterior surface is provided between the distal and proximal ends. A vibration generating drive mechanism with is provided. The vibration generating drive mechanism is provided within the handle. The vibration generating drive mechanism has a battery.

Operational components are provided on the handle. The operational components include an ON button. The operational components include an OFF button. The operational components also include an IN-USE light. The IN-USE light is provided on the exterior surface of the handle adjacent to the distal end. The operational components also include a vibrating coupler. The vibrating coupler is adapted to vibrate rapidly during use upon depressing the ON button.

Provided next is a coupling head. The coupling head is in a generally cylindrical configuration. The coupling head has an enlarged distal end. The coupling head has an enlarged proximal end. The coupling head has an exterior surface. The exterior surface is provided between the enlarged distal and enlarged proximal ends. The enlarged proximal end has a coupling recess. A vibrating coupler is provided. In this manner the coupling recess receives the vibrating coupler. The enlarged distal end has a planar surface forwardly. The enlarged distal end has a hemispherical surface rearwardly. The hemispherical surface has a transversely extending recess. The transversely extending recess is in a retentive configuration to removably receive and retain the holder, which exists as its reciprocal in shape.

Further provided is a replaceable holder. The replaceable holder has a central base. The central base has the reciprocal retentive shape of the rearwardly facing transverse recess to which the holder will be removably received. The replaceable holder has two outwardly extending fingers. The fingers have free ends. A piece of floss is provided. The piece of floss is secured between the free ends. The head and the holder are fabricated of a plastic material. The plastic material has limited flexibility and resilience. Applying pressure to the central base of the holder toward the retentive recess of the head will couple and secure the holder with respect to the head and whereby applying pressure to the free ends of the fingers will allow uncoupling of the holder with respect to the head. The fingers are spaced from each other by between 0.50 and 1.00 inches. The floss is spaced from the base of the holder by between 0.40 and 0.75 inches. In this manner the floss is allowed to be positioned between teeth being flossed with the teeth between the fingers.

Provided last are bristles. The bristles extend from the planar surface of the base between the fingers. The bristles have a length of between 0.125 and 0.250 inches. The bristles are adapted to contact ends of teeth being flossed. In this manner the bristles function as a stop to control the depth of penetration of the floss between the teeth while the ON button has been depressed and the head is vibrating during flossing.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved flossing system which has all of the advantages of the prior art teeth cleaning systems of known designs and configurations and none of the disadvantages.

It is another object of the present invention to provide a new and improved flossing system which may be easily and efficiently manufactured and marketed for both new handles with vibration generating drive mechanisms not currently on the market or otherwise known and existing handles with vibration generating drive mechanisms currently on the market.

It is further object of the present invention to provide a new and improved flossing system which is of durable and reliable constructions.

An even further object of the present invention is to provide a new and improved flossing system which is susceptible of a low cost of manufacture with regard to both materials and labor, and which accordingly is then susceptible of low prices of sale to the consuming public, thereby making such flossing system economically available to the buying public.

Even still another object of the present invention is to provide a flossing system for cleaning teeth at regions between adjacent teeth of a user and for vibrating regions of the mouth of the user between teeth and gums, the cleaning and vibrating being done in a safe, painless, convenient, efficient and economical manner.

Lastly, it is an object of the present invention to provide a new and improved flossing system. A handle has distal and proximal ends and an exterior surface. Controls with a vibrating coupler are adapted to vibrate rapidly in response to the controls. A head has a distal end and a proximal end. The proximal end has a coupling recess for receiving the vibrating coupler. The enlarged distal end has a generally planar surface and a generally hemispherical surface. The hemispherical surface has a recess to couple with a holder. A holder has a central base and two outwardly extending fingers. The fingers have free ends with a piece of floss secured between the free ends. Bristles extend from the planar surface between the fingers to control the movement of the floss between teeth.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a rear elevational view of the flossing system shown in FIG. 1.

FIG. 3 side elevational view of the system taken along line 3-3 of FIG. 2.

FIG. 4 is an enlarged end elevational view of the head of the system of the prior Figures.

FIG. 5 is an exploded enlarged end elevational view of the head of the system of FIG. 4.

The same reference numerals refer to the same parts throughout the various Figures.

DESCRIPTION OF THE PREFERRED EMBODIMENT

Figure 1:
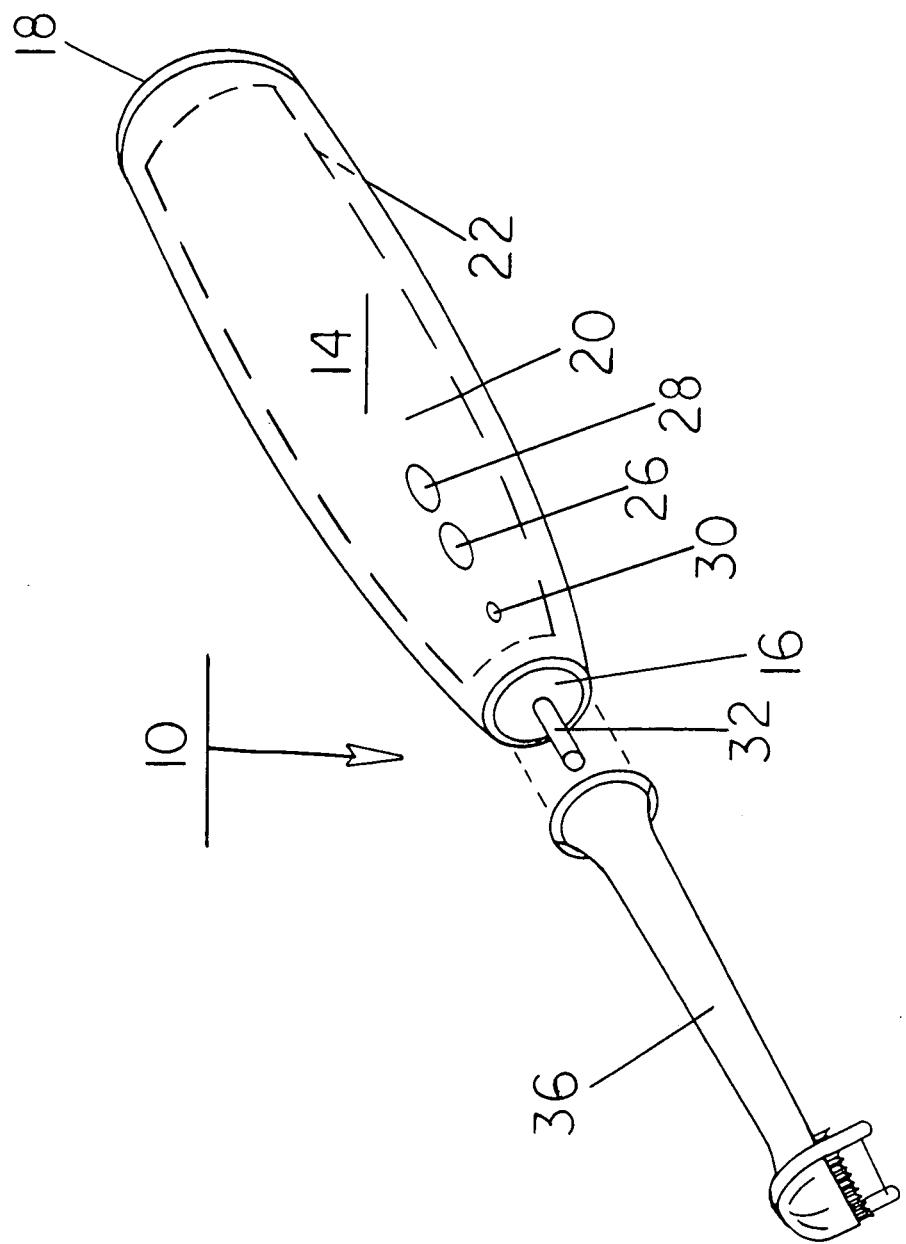
FIG. 1 is an exploded perspective illustration of a flossing system constructed in accordance with the principles of the present invention.

With reference now to the drawings, and in particular to FIG. 1 thereof, the preferred embodiment of the new and improved flossing system embodying the principles and concepts of the present invention and generally designated by the reference numeral 10 will be described.

The present invention, the flossing system 10 is comprised of a plurality of components. Such components in their broadest context include a handle, controls, a coupling head, a holder and bristles. Such components are individually configured and correlated with respect to each other so as to attain the desired objective.

First provided is a handle 14. The handle is in a generally cylindrical configuration. The handle has a distal end 16. The handle has a proximal end 18. The handle has an exterior surface 20. The exterior surface is provided between the distal and proximal ends. A vibration generating drive mechanism 22 with is provided. The vibration generating drive mechanism is provided within the handle. The vibration generating drive mechanism has a battery.

Operational components are provided on the handle. The operational components include an ON button 26. The operational components include an OFF button 28. The operational components also include an IN-USE light 30. The IN-USE light is provided on the exterior surface of the handle adjacent to the distal end. The operational components also include a vibrating coupler 32. The vibrating coupler is adapted to vibrate rapidly during use upon depressing the ON button.

Provided next is a coupling head 36. The head is in a generally cylindrical configuration. The head has an enlarged distal end 38. The head has an enlarged proximal end 40. The head has an exterior surface 42. The exterior surface is provided between the enlarged distal and enlarged proximal ends. The enlarged proximal end has a coupling recess 44. A vibrating coupler 32 is provided. In this manner the coupling recess. receives the vibrating coupler. The enlarged distal end has a planar surface forwardly. The enlarged distal end has a hemispherical surface rearwardly. The hemispherical surface has a transversely extending recess 46. The transversely extending recess is in a retentive configuration to removably receive and retain the replaceable holder 50, which exists as its reciprocal in shape.

Further provided is a replaceable holder 50. The replaceable holder has a central base 52. The central base has the reciprocal retentive shape of the rearwardly facing transverse recess 46 of the head to which the holder will be removably received. The replaceable holder has two outwardly extending fingers 54. The fingers have free ends. A piece of floss 56 is provided. The piece of floss is secured between the free ends. The head and the holder are fabricated of a plastic material. The plastic material has limited flexibility and resilience whereby applying pressure, note FIG. 5, to the central base of the holder toward the retentive recess 46 of the head will couple and secure the holder with respect to the head and whereby applying pressure in an opposite direction to the free ends of the fingers will allow uncoupling of the holder with respect to the head. The fingers are spaced from each other by between 0.50 and 1.00 inches. The floss is spaced from the base of the holder by between 0.40 and 0.75 inches. In this manner the floss is allowed to be positioned between teeth being flossed with the teeth between the fingers.

Provided last are bristles 60. The bristles extend from the planar surface of the base between the fingers. The bristles have a length of between 0.125 and 0.250 inches. The bristles are adapted to contact ends of teeth being flossed. In this manner the bristles function as a stop to control the depth of penetration of the floss between the teeth while the ON button has been depressed and the head is vibrating during flossing.

As may be seen in FIG. 4, the bristles constitute a stop extending from the planar surface of the base between the fingers. The stop has a length of between 0.125 and 0.250 inches. The stop is adapted to contact the surface of the teeth being flossed and to thereby function as a stop to control the depth of penetration of the floss between the teeth while the ON button has been depressed and the head is vibrating during flossing. The fingers are devoid of stops except for the stop extending from the planar surface of the base between the fingers. In this manner, lateral movement of the floss is limited solely by the fingers.

The releasable coupling between the recess 46 and the base 52 of the holder 50 is illustrated as being achieved through lines in a zig-zag or Z-shaped configuration. It should be understood, however, that the recess and the base of the holder could readily take any of a wide variety of complimentary configurations whereby they would still achieve their coupling and uncoupling function.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A flossing system (10) for cleaning teeth at regions between adjacent teeth of a user and for vibrating regions of the mouth of the user between teeth and gums, the cleaning and vibrating being done in a safe, painless, convenient, efficient and economical manner, the system consisting of: a handle (14) in a generally cylindrical configuration and having a distal end (16) and a proximal end (18) and an exterior surface (20) between the distal and proximal ends, a vibration generating drive mechanism (22) and a battery within the handle; operational components on the handle, the operational components including an ON button (26) and an OFF button (28) and an IN-USE light (30) on the exterior surface of the handle adjacent to the distal end, the operational components also including a vibrating coupler(32) adapted to vibrate rapidly during use upon depressing the ON button; a coupling head (36) in a generally cylindrical configuration and having an enlarged distal end (38) and an enlarged proximal end (40) and an exterior surface (42) between the enlarged distal and enlarged proximal ends, the enlarged proximal end being formed with a coupling recess (44) for receiving the vibrating coupler (32), the enlarged distal end being formed with a planar surface forwardly and a hemispherical surface rearwardly, the hemispherical surface being formed with a transversely extending coupling recess (46) in a retentive configuration to removably receive the central base (52) of the replaceable holder (50) existing as its reciprocal in shape; a replaceable holder (50) having a central base (52) and two outwardly extending fingers (54), the fingers having free ends with a piece of floss (56) secured between the free ends, the central base (52) having the reciprocal retentive shape of the rearwardly facing transverse recess (46) to which the holder will be removably received, the head and the holder being fabricated of a plastic material with flexibility and resilience whereby applying pressure to the central base of the holder toward the retentive recess (46) of the head will couple and secure the holder with respect to the head and whereby applying pressure in an opposite direction to the free ends of the fingers will allow uncoupling of the holder with respect to the head, the fingers being spaced from each other by between 0.50 and 1.00 inches, the floss being spaced from the base of the holder by between 0.40 and 0.75 inches, allowing the teeth to be placed between the fingers, the floss to be positioned between teeth, and thus the focused vibrating energy to effect the floss as its positioned between the teeth; and bristles (60) parallel with the floss extending from the planar surface of the base between the fingers, the bristles having a length of between 0.125 and 0.250 inches, the bristles are adapted to contact the surface of the teeth being flossed and to thereby function to control the depth of penetration of the floss between the teeth while the ON button has been depressed and the head is vibrating during flossing, the fingers being devoid of bristles except for the planar stop extending from the planar surface of the base between the fingers whereby lateral movement of the floss is limited solely by the fingers and not by bristles.

* * * * *